United States Patent [19]

Shepard

[11] Patent Number: 4,585,787

[45] Date of Patent: Apr. 29, 1986

[54] 5-[2(OR 3)-HYDROXYPHENYLSULFONYL]THIOPHENE-2-SULFONAMIDES FOR THE TOPICAL TREATMENT OF ELEVATED INTRAOCULAR PRESSURE

[75] Inventor: Kenneth L. Shepard, North Wales, Pa.

[73] Assignee: Merck & Co., Inc., Rahway, N.J.

[21] Appl. No.: 764,380

[22] Filed: Aug. 12, 1985

Related U.S. Application Data

[63] Continuation-in-part of Ser. No. 505,673, Jun. 20, 1983, Pat. No. 4,542,152, which is a continuation-in-part of Ser. No. 497,388, May 23, 1983, abandoned.

[51] Int. Cl.[4] .............................................. A61K 31/38
[52] U.S. Cl. ..................................... 514/445; 514/913
[58] Field of Search ................... 514/445, 913; 549/65

[56] References Cited

U.S. PATENT DOCUMENTS

| | | | |
|---|---|---|---|
| 4,029,809 | 7/1975 | Smith et al. | 424/275 |
| 4,386,098 | 5/1983 | Woltersdorf et al. | 424/270 |
| 4,416,890 | 5/1982 | Woltersdorf | 424/270 |
| 4,426,388 | 4/1982 | Woltersdorf | 548/166 |
| 4,454,148 | 12/1982 | Woltersdorf | 548/172 |
| 4,456,599 | 4/1983 | Woltersdorf | 548/114 |
| 4,477,466 | 5/1983 | Shepard | 544/124 |
| 4,499,103 | 3/1983 | DeSolms | 514/365 |
| 4,542,152 | 5/1983 | Shepard | 514/445 |

FOREIGN PATENT DOCUMENTS 0036351 9/1981 European Pat. Off. .
1459571 12/1976 United Kingdom .

OTHER PUBLICATIONS

Gelatt et al., Am. J. Vet. Res., 40, 334–345 (1979).
Havener, Ocular Pharmacology, pp. 395–416 (1966).

*Primary Examiner*—Douglas W. Robinson
*Attorney, Agent, or Firm*—William H. Nicholson; Michael C. Sudol

[57] ABSTRACT

5-[2(or 3)-Hydroxyphenylsulfonyl]thiophene-2-sulfonamides are useful for the topical treatment of elevated intraocular pressure. Ophthalmic compositions including drops and inserts are disclosed.

6 Claims, No Drawings

4,585,787

5-[2(OR 3)-HYDROXYPHENYLSULFONYL]THIOPHENE-2-SULFONAMIDES FOR THE TOPICAL TREATMENT OF ELEVATED INTRAOCULAR PRESSURE

SUMMARY OF THE INVENTION

This is a continuation-in-part of a co-pending application Ser. No. 505,673 filed June 20, 1983, now U.S. Pat. No. 4,542,152 which in turn is a continuation-in-part of application Ser. No. 497,388 filed May 23, 1983 (abandoned).

This invention relates to 5-[2(or 3)-hydroxyphenylsulfonyl]thiophene-2-sulfonamides, found to be useful in the reduction of elevated intraocular pressure. More particularly this invention relates to compositions including the compound of the structural formula:

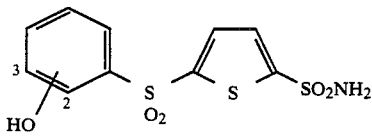

as well as the ophthalmologically acceptable salts thereof wherein the active entity is incorporated in an ophthalmologically suitable carrier therefor. This invention especially relates to methods for the treatment of elevated intraocular pressure, especially when accompanied by pathological damage such as in the disease known as glaucoma.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure.

Although pilocarpine and physostigmine increase the outflow of aqueous humor and thus reduce intraocular pressure, they have no effect on the biological mechanism largely responsible for aqueous humor formation, the carbonic anhydrase pathway. Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of exposing body carbonic anhydrase to their action. Such a potential gross disruption of a basic enzyme system is justified only during an acute attack of alarmingly elevated intraocular pressure, or when no other agent is effective. Despite the desireability of directing the carbonic anhydrase inhibitor only to the desired ocular target tissue, no topically effective carbonic anhydrase inhibitors are presently available for clinical use.

DESCRIPTION OF THE INVENTION

Compositions of 5-[2-(or 3-)hydroxyphenylsulfonyl]-thiophene-2-sulfonamides or ophthalmologically acceptable salts thereof are now found to inhibit carbonic anhydrase and, moreover, to lower intraocular pressure when topically administered to the mammalian eye, particularly in the form of drops or inserts. Examples of such ophthalmologically acceptable salts include the alkali metal salts.

A number of 5-[phenylsulfonyl(or sulfinyl)]thiophene-2-sulfonamides have been described in British Pat. No. 1,459,571 and *J. Med. Chem.*, 24, 959 (1981). Those that are active in the novel compositions of this invention have structural formula:

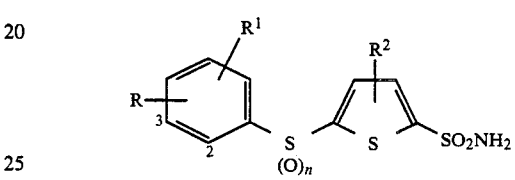

or an ophthalmologically acceptable salt thereof, wherein:

n is 1 or 2;
R is
 (1) —OH
 (2)

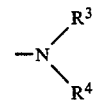

wherein $R^3$ and $R^4$ are independently selected from:
 (a) hydrogen,
 (b) $C_{1-3}$alkyl,
 (c) $C_{2-5}$alkanoyl,
 (d) $C_{3-6}$cycloalkylcarbonyl,
 (e) benzoyl,
 (f) $C_{1-3}$alkoxycarbonyl,
 (g) N—$C_{1-3}$alkyl carbamoyl,
 (h) $C_{1-3}$alkylsulfonyl,
 (3)

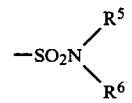

wherein $R^5$ and $R^6$ are independently selected from hydrogen, $C_{1-3}$ alkyl or $C_{3-6}$ cycloalkyl,
 (4) —$CH_2CO_2H$,
 (5)

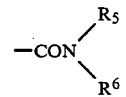

(6) —$CO_2H$, or
 (7)

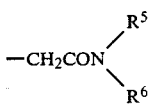

R[1] is
(1) hydrogen,
(2) halo, such as chloro, bromo or fluoro,
(3) $C_{1-3}$ alkyl or
(4) $C_{1-3}$ alkoxy; and R[2] is
(1) hydrogen, or
(2) halo, such as chloro or bromo.

A preferred embodiment of the compounds active in the novel compositions of this invention includes those compounds wherein:
n is 2;
R is OH in the 2- or 3-position and
R[1] and R[2] are both hydrogen.

Other representative species are those defined by the following table wherein n is 1 or 2:

| | R | R[1] | R[2] |
|---|---|---|---|
| 1 | 4-NHCOCH$_3$ | H | H |
| 2 | 4-NHCOC$_6$H$_5$ | H | H |
| 3 | 4-SO$_2$NH$_2$ | H | H |
| 4 | 4-NHCOC$_2$H$_5$ | H | H |
| 5 | 4-NHCOCH$_3$ | 2-Cl, 5-CH$_3$ | H |
| 6 | 4-NHSO$_2$CH$_3$ | H | H |
| 7 | 4-NHCOOCH$_3$ | H | H |
| 8 | 3-NHCOCH$_3$ | 4-OCH$_3$ | H |
| 9 | 4-CH$_2$COOH | H | H |
| 10 | 4-CH$_2$CONHCH$_3$ | H | H |
| 11 | 4-NHCONHCH$_3$ | H | H |
| 12 | 4-NHCOCH$_3$ | 3-Cl | H |
| 13 | 4-NHCOCH$_3$ | H | 4-Br |
| 14 | 4-NHCOCH$_3$ | H | 3-Cl |
| 15 | 4-NHCOCH(CH$_3$)$_2$ | H | H |
| 16 | 4-NHCOCH$_2$CH$_2$CH$_3$ | H | H |
| 17 | 4-NHCOC(CH$_3$)$_3$ | H | H |
| 18 | 4-NHCOCH$_3$ | H | 4-Cl |
| 19 | 4-NHCOCH$_3$ | H | 3-Br |
| 20 | 3-NHCOOC$_2$H$_5$ | H | H |
| 21 | 4-NHCO | H | H |
| 22 | 4-CONH$_2$ | H | H |
| 23 | 3-CO$_2$H | H | H |
| 24 | 3-CONH$_2$ | H | H |
| 25 | 3-CONHCH$_3$ | H | H |
| 26 | 3-CONHCH(CH$_3$)$_2$ | H | H |
| 27 | 4-CH$_2$CONH$_2$ | H | H |
| 28 | 2-CONH$_2$ | H | H |
| 29 | 3-NHCOCH$_3$ | H | H |
| 30 | 4-OH | H | H |
| 31 | 4-CH$_2$CONHC(CH$_3$)$_3$ | H | H |
| 32 | 3-CONH | H | H |

The most preferred species is 5-[(4-hydroxyphenyl)-sulfonyl]thiophene-2-sulfonamide, claimed in parent application Ser. No. 505,673 filed June 20, 1983.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quarternary ammonium compounds, phenylmercuric salts known to have cold sterilizing properties and which are non-injurious in use, thimerosal, methyl and propyl paraben, benzyl alcohol, phenylethanol, buffering ingredients such as sodium chloride, sodium borate, sodium acetate, gluconate buffers, and other conventional ingredients such as sorbitan monolaurate, triethanolamine oleate, polyoxyethylene sorbitan monopalmitate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles, aqueous gel vehicles and the like. Generally, the drug is present in such vehicles in an amount of from 0.1 to about 25% by weight or more. Preferably the drug is present in an amount of from 0.1 to 15% by weight, and most preferably from 0.25 to 5% by weight.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodible insert, i.e. one which after dispensing the drug remains essentially intact, or a bioerodible insert, i.e. one that either is soluble in lacrimal fluids, or otherwise disintegrates. While the inert employed is not critical, those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the insert described below is found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

The following examples of ophthalmic formulations are given by way of illustration.

EXAMPLE 1

| Solution Composition | a | b |
|---|---|---|
| 5-[(2-Hydroxyphenyl)sulfonyl]-thiophene-2-sulfonamide (I) | 1 mg. | 15 mg. |
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |

| -continued | | |
|---|---|---|
| Solution Composition | a | b |
| Water for injection q.s. ad. | 1.0 ml. | 1.0 ml. |

Compound I, phosphate buffer salts, and benzalkonium chloride are added to and admixed with water. The pH of the resulting admixture is adjusted to 6.8 and the final formulation diluted to volume. The formulation is rendered sterile by appropriate means, such as starting the preparative procedure with sterile components and proceeding under sterile conditions, irradiating or autoclaving the finished formulation, or the like.

EXAMPLE 2

| 5-[(3-Hydroxyphenyl)sulfonyl]-thiophene-2-sulfonamide (I) | 5 mg. |
|---|---|
| petrolatum q.s. ad. | 1 gram |

Compound I and the petrolatum are aseptically combined.

EXAMPLE 3

| 5-[(3-Hydroxyphenyl)sulfonyl]-thiophene-2-sulfonamide | 1 mg |
|---|---|
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 4

| 5-[(2-Hydroxyphenyl)sulfonyl]-thiophene-2-sulfonamide | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 5

| 5-[(3-Hydroxyphenyl)sulfonyl]-thiophene-2-sulfonamide | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 6

Aqueous Gel

| 5-[(3-Hydroxyphenyl)sulfonyl]-thiophene-2-sulfonamide | 1 mg |
|---|---|
| Water | 99 mg |
| Carbopol 934 (B.F. Goodrich, Cleveland) | 1 mg |

EXAMPLE 7

| 5-[(2-Hydroxyphenyl)sulfonyl]-thiophene-2-sulfonamide | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

The drops, heretofore described in Example 1, are used in the usual way employing one to two drops per eye per patient per day. When inserts are employed usually one insert per patient per eye per day is satisfactory. Elevated intraocular pressure is a condition that must be carefully monitored on an individual basis. Thus an intraocular pressure lowering amount can be as little as 0.001–0.01 mg to as much as 0.100–0.250 mg per eye per patient per day of active medicament. As the individual differences between patient drug response are encountered and as experience with the medicament increases and information accumulates because of a larger patient population being developed, the daily ocular dose for the median population group can be stated with greater statistical accuracy. It may well be found that only a few patients respond to the minimal dose, and then only for a transient period. Also only a few patients may require administration of the drug at the higher dosage ranges. The dose also may be divided for administration. Thus, the quantities set forth previously can be administered in a course of individual deliveries comprising 1–4 or more times per day.

The concentration of active drug in any formulation can vary within a wide range. Clearly, as a function of concentration, the desired dose of formulation will consequently vary for example from a single drop or insert or multiple drops or inserts or larger or smaller inserts.

What is claimed is:

1. A method for treating elevated intraocular pressure which comprises topically applying to an eye in need of such treatment an effective intraocular pressure lowering amount of a carbonic anhydrase inhibitor of the formula:

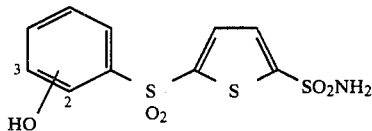

or an ophthalmologically acceptable salt thereof, wherein:

the —OH in the 2- or 3-position.

2. The method according to claim 1 wherein the carbonic anhydrase inhibitor is administered in a polymeric insert.

3. The method according to claim 2 where said insert comprises from 0.01 to 25% by weight of the carbonic anhydrase inhibitor.

4. The method according to claim 1 wherein the carbonic anhydrase inhibitor is administered in an ointment base.

5. The method according to claim 1 wherein the carbonic anhydrase inhibitor is administered in a liquid vehicle.

6. The method according to claim 1 wherein the carbonic anhydrase inhibitor is administered in an aqueous gel.

* * * * *